US009340518B2

(12) United States Patent
Herse

(10) Patent No.: US 9,340,518 B2
(45) Date of Patent: May 17, 2016

(54) PROCESS FOR THE PREPARATION OF (2Z,5Z)-5-(3-CHLORO-4-((R)-2,3-DIHYDROXYPROPDXY)BENZYLIDENE)-2-(PROPYLIMINO)-3-(O-TOLYL) THIAZOLIDIN-4-ONE AND INTERMEDIATE USED IN SAID PROCESS

(71) Applicant: Actelion Pharmaceuticals, LTD, Allschwil (CH)

(72) Inventor: Christelle Herse, Visp (CH)

(73) Assignee: ACTELION PHARMACEUTICALS LTD., Allschwil (CH)

(*) Notice: Subject to any disclaimer, the term of this patent is extended or adjusted under 35 U.S.C. 154(b) by 0 days.

(21) Appl. No.: 14/422,167

(22) PCT Filed: Aug. 15, 2013

(86) PCT No.: PCT/IB2013/056662
§ 371 (c)(1),
(2) Date: Feb. 17, 2015

(87) PCT Pub. No.: WO2014/027330
PCT Pub. Date: Feb. 20, 2014

(65) Prior Publication Data
US 2015/0203459 A1 Jul. 23, 2015

(30) Foreign Application Priority Data

Aug. 17, 2012 (EP) .................................... 12180920

(51) Int. Cl.
| C07C 45/64 | (2006.01) |
| C07C 45/81 | (2006.01) |
| C07C 47/575 | (2006.01) |
| C07D 277/54 | (2006.01) |

(52) U.S. Cl.
CPC .............. *C07D 277/54* (2013.01); *C07C 45/64* (2013.01); *C07C 45/81* (2013.01); *C07C 47/575* (2013.01); *C07B 2200/13* (2013.01)

(58) Field of Classification Search
CPC ........ C07C 45/64; C07C 45/81; C07C 47/575
See application file for complete search history.

(56) References Cited

U.S. PATENT DOCUMENTS

| 3,077,402 | A | 2/1963 | Blout Elkan et al. |
| 3,175,905 | A | 3/1965 | Stahlhofen |
| 3,759,938 | A | 9/1973 | Giraudon |
| 5,422,360 | A | 6/1995 | Miyajima et al. |
| 5,677,322 | A | 10/1997 | Yasumura et al. |
| 6,353,006 | B1 | 3/2002 | Dixon et al. |
| 6,380,229 | B1 | 4/2002 | Yoneda et al. |
| 7,435,828 | B2 | 10/2008 | Binkert et al. |
| 7,626,037 | B2 | 12/2009 | Binkert et al. |
| 7,767,701 | B2 | 8/2010 | Hasegawa et al. |
| 7,875,726 | B2 | 1/2011 | Binkert et al. |
| 7,879,821 | B2 | 2/2011 | Hauser et al. |
| 7,892,354 | B2 | 2/2011 | Blatter |
| 8,263,780 | B2 | 9/2012 | Abele et al. |
| 8,273,779 | B2 | 9/2012 | Binkert et al. |
| RE43,728 | E | 10/2012 | Binkert et al. |
| RE43,833 | E | 11/2012 | Binkert et al. |
| 8,524,752 | B2 | 9/2013 | Binkert et al. |
| 8,785,484 | B2 | 7/2014 | Brossard et al. |
| RE45,174 | E | 9/2014 | Binkert et al. |
| 8,912,340 | B2 | 12/2014 | Abele et al. |
| 9,000,018 | B2 | 4/2015 | Binkert et al. |
| 9,062,014 | B2 | 6/2015 | Bonham et al. |
| 2004/0009527 | A1 | 1/2004 | Dong et al. |
| 2004/0167192 | A1 | 8/2004 | Solow-Cordero et al. |
| 2005/0019825 | A9 | 1/2005 | Dong et al. |
| 2005/0096364 | A1 | 5/2005 | Romine et al. |
| 2007/0249599 | A1 | 10/2007 | Duffy et al. |
| 2010/0160259 | A1 | 6/2010 | Schmouder et al. |
| 2011/0039818 | A1 | 2/2011 | Legangneux et al. |
| 2011/0257133 | A1 | 10/2011 | Schmouder et al. |
| 2014/0303217 | A1 | 10/2014 | Brossard et al. |
| 2014/0315964 | A1 | 10/2014 | Brossard et al. |
| 2014/0316140 | A1 | 10/2014 | Brossard et al. |
| 2015/0265580 | A1 | 9/2015 | Brossard et al. |

FOREIGN PATENT DOCUMENTS

| EP | 1 219 612 | 7/2002 |
| GB | 999796 | 7/1965 |

(Continued)

OTHER PUBLICATIONS

Anonymous, "Actelion's Orally Active Selective S1P1 Receptor Agonist to be Jointly Developed/Promoted with Roche in Autoimmune Disorders and Transplantation Deal Potentially Worth Well Over US $630 Million to Actelion", Muscoskeletal Report, [Online], Jul. 20, 2006, pp. 1, New York, NY 10016, USA, Retrieved from the Internet: URL: http://www.mscreport.com/print.cfm?articleID=827>.
B. Rodriguez-Spong et al; "General principles of pharmaceutical solid polymorphism: a supramolecular perspective"; Advanced Drug Delivery Reviews, 2004, 56, pp. 241-274.
Background Information for the October ACCPS Meeting, FDA, 2002.
Bailar et al; The New England Journal of Medicine; 1997; Massachusetts Medical Society, vol. 336, Issue 22, pp. 1569-1574.
Baker; Journal of Applied Physiology; 2002; American Physiological Society; vol. 92; pp. 1779-1780.
Beger et al; World Journal of Surgery; 2003; Societe Internationale de Chirugie; vol. 27; pp. 1075-1084.
Berge et al; "Pharmaceutical Salts"; Journal of Pharmaceutical Sciences; vol. 66, No. 1; 1977; pp. 1-19.
Bolli et al; Journal of Medicinal Chemistry 2010; vol. 53, No. 10 pp. 4198-4211.
*Supporting Information* to Bolli et al; Journal of Medicinal Chemistry; 2010; 53(10); 4198-4211.
Braga et al; "Dealing with Crystal Forms (The Kingdom of Serendip?)", Chemistry, An Asian Journal, vol. 6, pp. 2214-2223 (2011).
Braun-Moscovici et al; Current Opinion in Rheumatology; 2002; Lippincott Williams and Wilkins; vol. 14; pp. 711-716.

(Continued)

*Primary Examiner* — Matthew Coughlin
(74) *Attorney, Agent, or Firm* — Hoxie & Associates LLC

(57) ABSTRACT

The present invention relates to a new process for the preparation of (2Z,5Z)-5-(3-chloro-4-((R)-2,3-dihydroxypropoxy)benzylidene)-2-(propylimino)-3-(o-tolyl)thiazolidin-4-one and to the new intermediate (R)-3-chloro-4-(2,3-dihydroxypropoxy)-benzaldehyde used in this process. (2Z, 5Z)-5-(3-Chloro-4-((R)-2,3-dihydroxypropoxy) benzylidene)-2-(propylimino)-3-(o-tolyl)thiazolidin-4-one is described in WO 2005/054215 to act as an immunosuppressive agent. The present invention further also relates to a new process for the preparation of (R)-3-chloro-4-(2,3-dihydroxypropoxy)-benzaldehyde.

18 Claims, 1 Drawing Sheet

(56) References Cited

FOREIGN PATENT DOCUMENTS

| GB | 1001479 | 8/1965 |
|---|---|---|
| IL | 198847 | 5/2009 |
| IL | 208154 | 9/2010 |
| JP | 2007-511563 | 5/2007 |
| WO | WO 91/17151 | 11/1991 |
| WO | WO 96/20936 | 7/1996 |
| WO | WO 2004/007491 | 1/2004 |
| WO | WO 2004/010987 | 2/2004 |
| WO | WO 2005/054215 | 6/2005 |
| WO | WO 2005054215 A1 * | 6/2005 |
| WO | WO 2005/123677 | 12/2005 |
| WO | WO 2006/010544 | 2/2006 |
| WO | WO 2006/058316 | 6/2006 |
| WO | WO 2006/094233 | 9/2006 |
| WO | WO 2006/100631 | 9/2006 |
| WO | WO 2006/100633 | 9/2006 |
| WO | WO 2006/100635 | 9/2006 |
| WO | WO 2006/137019 | 12/2006 |
| WO | WO 2007/060626 | 5/2007 |
| WO | WO 2007/080542 | 7/2007 |
| WO | WO 2007/086001 | 8/2007 |
| WO | WO 2008/029306 | 3/2008 |
| WO | WO 2008/029370 | 3/2008 |
| WO | WO 2008/029371 | 3/2008 |
| WO | WO 2008/035239 | 3/2008 |
| WO | WO 2008/062376 | 5/2008 |
| WO | WO 2008/114157 | 9/2008 |
| WO | WO 2009/024905 | 2/2009 |
| WO | WO 2009/115954 | 9/2009 |
| WO | WO 2010/046835 | 4/2010 |
| WO | WO 2010/065760 | 6/2010 |
| WO | WO 2010/072703 | 7/2010 |
| WO | WO 2010/075239 | 7/2010 |

OTHER PUBLICATIONS

Brinkmann, V. "Sphingosine 1-Phosphate Receptors in Health and Disease: Mechanistic Insights from Gene Deletion Studies and Reverse Pharmacology", Pharmacol. Ther. (2007), vol. 115, pp. 84-105.
Bunemann et al; "Activation of Muscarinic K+ Current in Guinea-Pig Atrial Myocytes by Sphingosine-1-phosphate", Journal of Physiology, vol. 489, pp. 701-707, (1995).
Byrn, et al; "Pharmaceutical Solids: A Strategic Approach to Regulator Consideration" Pharmaceutical Research, vol. 12, No. 7, pp. 945-954, (1995).
Caira, M.R., "Crystalline Polymorphism of Organic Compounds". Topics in Current Chemistry, vol. 198, pp. 163-208 (1998).
Carter et al; "Photochemically enhanced Binding of Samll Molecules to the Tumor Necrosis Factor Receptor-1 Inhibits the binding of TNF-alpha"; PNAS. vol. 98, No. 21, Oct. 9, 2001; pp. 11879-11884.
Davidov et al; "Chronic Nitric Oxide Synthase Blockade Desensitizes the Heart to the Negative Metabolic Effects of Nitric Oxide", Life Sciences, Pergamon Press, Oxford, GB, vol. 79, pp. 1674-1680, (2006).
Ellis et al; The New England Journal of Medicine, 2001, Massachusetts Medical Society, vol. 345, No. 4, pp. 248-255.
Ehrlenmeyer et al; "Structural Chemical Investigations. VII. Reactive Behavior of Thiourea to Unsaturated Acids"; CA 37:10142, 1943.
Frolkis et al; "The Role of 'Invertors' (Intracellular Activators) in Age-related Changes in Cell Response to Hormones", Experimental Gerontology, vol. 30, pp. 401-414, (1995).
Fujishiro et al; "Use of Sphingosine-1-Phosphate 1 Receptor Agonist, KRP-203, in Combination with a Subtherapeutic Dose of Cyclosporine A for Rat Renal Transplantation", Transplantation, vol. 82(6), pp. 804-812, (2006).
Gibson; "Pharmaceutical Preformulation of Formulation"; HIS Health Group, Englewood, CO, USA 2001; Table of Contents.
Giese et al; Journal of Cancer Research and Clinical Oncology; 2001; Springer-Verlag; vol. 127, pp. 217-225.
Gould et al; "Salt Selections for Basic Drugs"; Int. J. Pharm.; vol. 33; 1986; pp. 201-217.
Grant, et al., "Polymorphism in Pharmaceutical Solids", (Chapter 1), pp. 1-10 (1999).
Guillory, "Polymorphism in Pharmacetical Solids" (Chapter 5), pp. 183-226, (1999).
Guo et al; "Effects of Sphingosine 1-phosphate on Pacemaker Activity in Rabbit Sino-atrial Node Cells", Pflugers Arch, vol. 438, pp. 642-648, (1999).
Hale et al; "Selecting Against S1P3 Enhances the Acute Cardiovascular Tolerability of 3-(N-benzyl)aminopropylphosphonic Acid S1P Receptor Agonists", Bioorganic & Medicinal Chemistry Letters, vol. 14(13), pp. 3501-3505, (2004).
Hilfiker, R. Polymorphism in the Pharmaceutical Industry, Wiley, 2006, 213-216.
Himmel et al; "Evidence for Edg-3 Receptor-Mediated Activation of IK.Ach by Sphingosine-1-Phosphate in Human Atrial Cardiomyocytes", Molecular Pharmacology, vol. 58, pp. 449-454, (2000).
Huwiler et al; "New Players on the Center Stage: Sphingosine 1-Phosphate and its Receptors as Drug Targets", Biochemical Pharmacology, Pergamon Press, Oxford, GB, vol. 75, pp. 1893-1900, doi:10.1016/j.bcp.2007.12.018, (2008).
Janusz et al; "New Cyclooxygenase-2/5-Lipoxyfenase Inhibitors. 3. 7-tert-Butyl-2,3-dihydro-3, 3-dimethylbenzofuran Derivatives as Gastrointestinal Safe Antiinflammatory and Analgesic Agents: Variations at the 5 Position"; J. Medicinal Chemistry, vol. 41, 1998, pp. 3515-3529.
Jones G. The Knoevenagel Condensation, 1967; pp. 204-273.
Kappos et al; "Oral Fingolimod (FTY720) for Relapsing Multiple Sclerosis", The New England Journal of Medicine, vol. 355(11), pp. 1124-1140, (2006).
Keller et al; Immunomodulator FTY720 Induces Myofibroblast Differentiation via the Lysophospholipid Receptor S1P3 and Smad3 Signaling, The American Journal of Pathology, vol. 170 (1), pp. 281-292 (2007).
Klika et al; "Regioselective Synthesis of 2-imino-1,3-thiazolidin-4-ones by Treatment of N-(Anthracen-9-yl)-N9-ehylthiourea [. . .]" Eur. J. Org. Chem. 2002, pp. 1248-1255.
Kovarik et al; "A Mechanistic Study to Assess Whether Isoproterenol can Reverse the Negative Chronotropic Effect of Fingolimod", Journal of Clinical Pharmacology, vol. 48, No. 3, pp. 303-310, Published on Jan. 24, 2008 as doi:10.1177/0091270007312903, (2008).
Koyrakh et al; "The Heart Rate Decrease Caused by Acute FTY720 Administration is Mediated by the G Protein-Gated Potassium Channel IKACh", American Journal of Transplantation, vol. 5, pp. 529-536, (2005).
Ma; "High-Affinity Activators of Cystic Fibrosis Transmembrance Conductance Regulator (CFTR) Chloride Conductance Identified by High-Throughput Screening"; The Journal of Biological Chemistry, vol. 277, No. 40, Issue of Oct. 4, pp. 37235-37241; [2002].
March; Advanced Organic Chemistry, Reactions, Mechanism an Structure, 3rd edition, 1985, pp. 342-343.
Martinet et al; Journal of the National Cancer Institute; 2000; National Cancer Institute; vol. 92; No. 11; pp. 931-936.
Maruzen, "Yuki Kagobutsu Kessyo Sakusei Handobukku (Handbook of Organic Compound Crystal Production)", p. 57-84 (2008) (See English Translation of Relevant Parts).
Non-Final Office Action dated Feb. 1, 2011, U.S. Appl. No. 12/516,0555.
Notices of Allowance dated Jul. 21, 2011, Nov. 15, 2011, and May 3, 2012, U.S. Appl. No. 12/516,055.
Ochi et al; "Sphingosine-1-Phosphate Effects on Guinea Pig Atrial Myocytes: Alterations in Action Potentials and K+ Currents", Cardiovascular Research, vol. 70, pp. 88-96, (2006).
Ottana et al; 5-Arylidene-2-imino-4-thiazolidinones: Design and Synthesis of Novel Anti-Inflammatory Agents, Bioorganic and Medicinal Chemistry, 13(13) (2005) pp. 4243-4252. (available online May 17, 2005).
Peters et al; "Sphingosine-1-Phosphate Signaling in the Cardiovascular System", Current Opinion in Pharmacology, vol. 7(2), pp. 186-192, doi:10.1016/j.coph.2006.09.008 (2007).
Pharm. Tech. Japan., Ch. 18, vol. 10, pp. 1629-1644, (2002) (see Engl. Translation of Relevant Parts).

(56) References Cited

OTHER PUBLICATIONS

Prout, et al; Catalyst Study of the Knoevengal Condensation vol. 8, No. 4, 1963, pp. 597-599.
Remington; "The Science and Practice of Pharmacy"; 20th Edition; Philadelphia College of Pharmacy and Science; 2003; Table of Contents.
Remington; "The Science and Practice of Pharmacy"; 21st Edition; Part 5, "Pharmaceutical Manufacturing" [published by Lippincott Williams & Wilkins] 2005; Table of Contents.
Sanna et al; "Sphingosine 1-Phosphate (S1P) Receptor Subtypes S1P1 and S1P3, Respectively, Regulate Lymphocyte Recirculation and Heart Rate", The Journal of Biological Chemistry, vol. 279(14), pp. 13839-13848, 2004.
Schmouder et al; "FTY720: Placebo-Controlled Study of the Effect on Cardiac Rate and Rhythm in Healthy Subjects" Journal of Clinical Pharmacology, vol. 46, pp-895-904, 2006.
Smith et al; Annals of Neurology; 2003; American Neurological Association; vol. 54; pp. 186-196.
Surh; Nature Reviews Cancer; 2003; Nature Publishing Group; vol. 3; pp. 768-780.
Written Opinion of PCT/IB2009/054592, dated Apr. 20, 2011.

\* cited by examiner

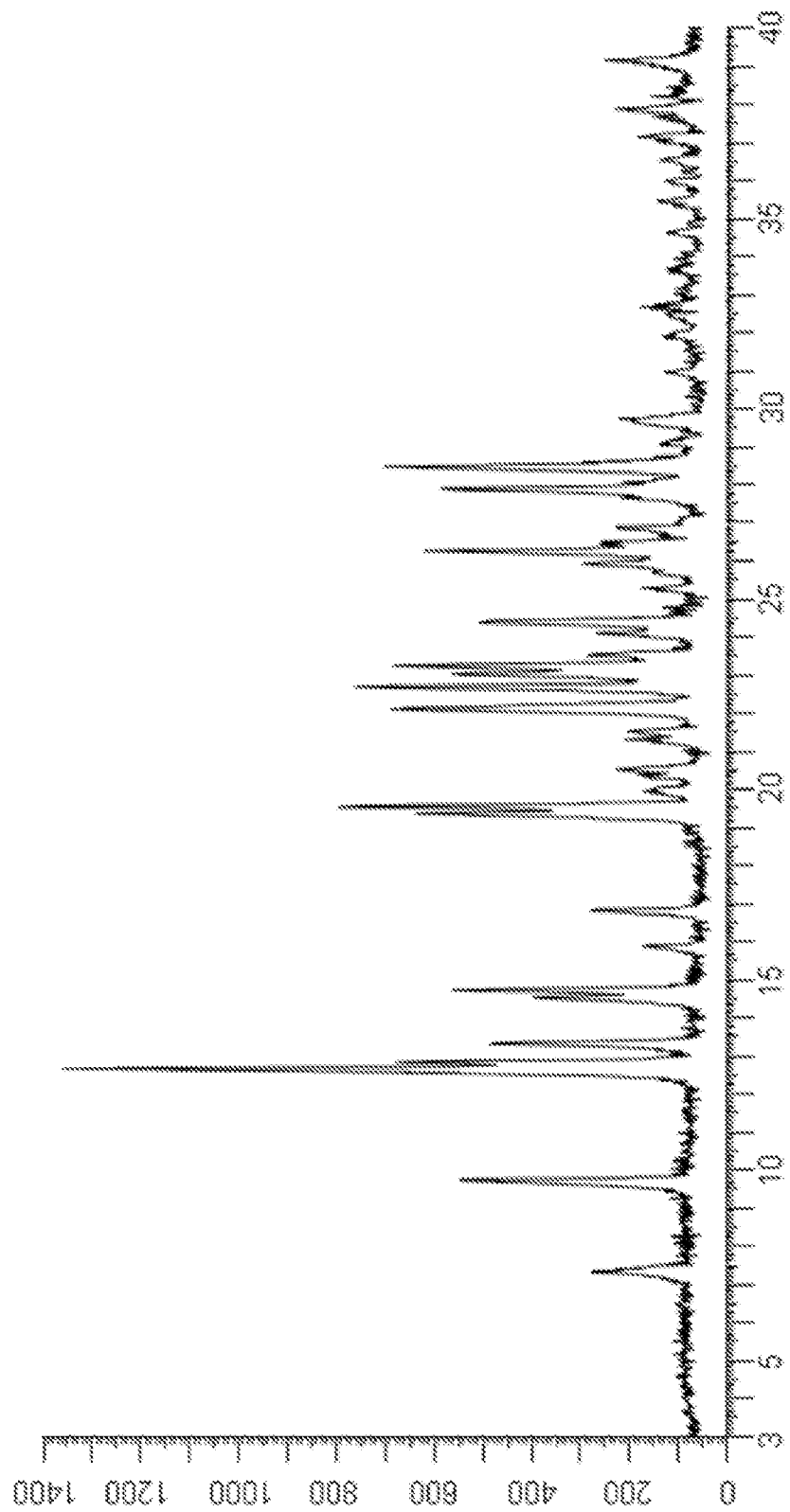

PROCESS FOR THE PREPARATION OF (2Z,5Z)-5-(3-CHLORO-4-((R)-2,3-DIHYDROXYPROPDXY)BENZYLIDENE)-2-(PROPYLIMINO)-3-(O-TOLYL)THIAZOLIDIN-4-ONE AND INTERMEDIATE USED IN SAID PROCESS

CROSS REFERENCE TO RELATED APPLICATIONS

This application is a U.S. National Phase Application filed under 35 U.S.C. 371 of International Application No. PCT/IB2013/056662, filed on Aug. 15, 2013, which claims the benefit of European Patent Application 12180920.6, filed on Aug. 17, 2012, the contents of each of which are herein incorporated by reference in their entirety.

FIELD OF THE INVENTION

The present invention relates to a new process for the preparation of (2Z,5Z)-5-(3-chloro-4-((R)-2,3-dihydroxypropoxy)benzyl idene)-2-(propylimino)-3-(o-tolyl)thiazolidin-4-one and to the new intermediate (R)-3-chloro-4-(2,3-dihydroxypropoxy)-benzaldehyde used in this process. (2Z,5Z)-5-(3-Chloro-4-((R)-2,3-dihydroxypropoxy)benzylidene)-2-(propylimino)-3-(o-tolyl)thiazolidin-4-one is described in WO 2005/054215 to act as an immunosuppressive agent. The present invention further also relates to a new process for the preparation of (R)-3-chloro-4-(2,3-dihydroxypropoxy)-benzaldehyde.

DESCRIPTION OF THE INVENTION

The present invention relates inter alia to a new process for the preparation of (2Z,5Z)-5-(3-chloro-4-((R)-2,3-dihydroxypropoxy)benzylidene)-2-(propylimino)-3-(o-tolyl)thiazolidin-4-one (hereinafter also referred to as the "COMPOUND" or "compound (2)"), especially in crystalline form C which form is described in WO 2010/046835. The preparation of COMPOUND and its activity as immunosuppressive agent is described in WO 2005/054215. Furthermore, WO 2008/062376 describes a new process for the preparation of (2Z,5Z)-5-(3-chloro-4-hydroxy-benzylidene)-2-propylimino-3-o-tolyl-thiazolidin-4-one which can be used as an intermediate in the preparation of COMPOUND.

Example 1a) below describes such a process of preparing (2Z,5Z)-5-(3-chloro-4-hydroxy-benzylidene)-2-propylimino-3-o-tolyl-thiazolidin-4-one according to WO 2008/062376. According to WO 2008/062376 the obtained (2Z,5Z)-5-(3-chloro-4-hydroxy-benzylidene)-2-propylimino-3-o-tolyl-thiazolidin-4-one can then be transformed into COMPOUND by using standard methods for the alkylation of phenols. Such an alkylation is described in Example 1b) below. Unfortunately, this process leads to the impurity (2Z,5Z)-5-(3-chloro-4-((1,3-dihydroxypropan-2-yl)oxy)benzylidene)-2-(propylimino)-3-(o-tolyl)thiazolidin-4-one which is present in about 2% w/w in the crude product (see Table 1) and up to 6 recrystallisations are necessary in order to get this impurity below 0.4% w/w (see Tables 1 and 2) which is the specified limit based on its toxicological qualification.

TABLE 1

| | IPC (area %) | Crude (w/w %) | I (w/w %) | II (w/w %) | III (w/w %) | IV (w/w %) | V (w/w %) |
|---|---|---|---|---|---|---|---|
| Experiment A | 3.0% | 1.82 | 1.20 (−34%) | 0.85 (−29%) | 0.59 (−31%) | 0.46 (−22%) | 0.34 (−26%) |
| Experiment B | 3.0% | 1.82 | 1.21 (−33%) | 0.87 (−28%) | 0.64 (−26%) | 0.46 (−28%) | 0.36 (−22%) |
| Experiment C | 3.0% | 1.79 | 1.23 (−31%) | 0.87 (−29%) | 0.63 (−28%) | 0.47 (−26%) | 0.35 (−26%) |

Table 1: Levels of the impurity (2Z,5Z)-5-(3-chloro-4-((1,3-dihydroxypropan-2-yl)oxy)benzylidene)-2-(propylimino)-3-(o-tolyl)thiazolidin-4-one as determined by HPLC obtained when preparing and purifying COMPOUND (approx. 10 g scale) according to Example 1 below. In the second and third column the values are provided which are observed before (IPC) and after (Crude) the first crystallisation, respectively, in a process according to Example 1b). In the last five columns the values are provided which are observed after recrystallisations I-V according to Example 1c).

TABLE 2

| | Recrystallisations | | | | | |
|---|---|---|---|---|---|---|
| | I (w/w %) | II (w/w %) | III (w/w %) | IV (w/w %) | V (w/w %) | VI (w/w %) |
| Batch 1 | 1.15 | 0.86 | 0.65 | 0.51 | 0.41 | 0.29 |
| Batch 2 | 1.26 | 0.88 | 0.67 | 0.49 | 0.42 | 0.3 |
| Batch 3 | 1.24 | 0.9 | 0.7 | 0.56 | 0.43 | 0.31 |
| Batch 4 | 1.24 | 1.26 | 0.85 | 0.7 | 0.53 | 0.41 |
| Average | 1.22 | 0.98 | 0.72 | 0.57 | 0.45 | 0.33 |

Table 2: Levels of the impurity (2Z,5Z)-5-(3-chloro-4-((1,3-dihydroxypropan-2-yl)oxy)benzylidene)-2-(propylimino)-3-(o-tolyl)thiazolidin-4-one as determined by HPLC obtained during purification of the COMPOUND via recrystallisations I-VI according to below Example 1c) (scale up to approx. 25 kg).

If, on the other hand, the phenolic alkylation is performed before the Knoevenagel condensation, i.e. before the reaction of the benzaldehyde with 2-[(Z)-propylimino]-3-o-tolyl-thiazolidin-4-one, as in Examples 2 and 3 below, then the analogous impurity 3-chloro-4-((1,3-dihydroxypropan-2-yl)oxy)benzaldehyde is being formed as well, which subsequently leads to the impurity (2Z,5Z)-5-(3-chloro-4-((1,3-dihydroxypropan-2-yl)oxy)benzylidene)-2-(propylimino)-3-(o-tolyl)thiazolidin-4-one in the next step, namely the Knoevenagel condensation. However, surprisingly the impurity 3-chloro-4-((1,3-dihydroxypropan-2-yl)oxy)benzaldehyde can be easily removed from (R)-3-chloro-4-(2,3-dihydroxypropoxy)-benzaldehyde via crystallisation (see Table 3), allowing a much more efficient and economical process for the preparation of COMPOUND compared to the process as described in WO 2008/062376.

TABLE 3

| | IPC result (area %) | After 1st crystallisation (area %) |
|---|---|---|
| Step 1/Batch 21 | 4.5 | 0.15 |
| Step 1/Batch 22 | 4.6 | 0.16 |

TABLE 3-continued

|  | IPC result (area %) | After 1st crystallisation (area %) |
|---|---|---|
| Step 1/Batch 23 | 4.2 | 0.24 |
| Step 1/Batch 24 | 4.5 | 0.20 |

Table 3: Levels of the impurity 3-chloro-4-((1,3-dihydroxypropan-2-yl)oxy)benzaldehyde as determined by HPLC before (IPC results, second column) and after the first crystallisation (third column) when using a process according to Example 3 (see below).

Table 4 shows that very low levels of the impurity (2Z,5Z)-5-(3-chloro-4-((1,3-dihydroxypropan-2-yl)oxy)benzylidene)-2-(propylimino)-3-(o-tolyl)thiazolidin-4-one are reached after only 1 recrystallisation if the (R)-3-chloro-4-(2,3-dihydroxypropoxy)-benzaldehyde obtained according to the process of the present invention is reacted with 2-[(Z)-propylimino]-3-o-tolyl-thiazolidin-4-one according to Example 4 below.

TABLE 4

|  | Impurity (w/w %) |
|---|---|
| Step 2/Batch 21 | 0.05 |
| Step 2/Batch 22 | 0.08 |
| Step 2/Batch 23 | 0.09 |
| Step 2/Batch 24 | 0.1 |

Table 4: Levels of the impurity (2Z,5Z)-5-(3-chloro-4-((1,3-dihydroxypropan-2-yl)oxy)benzylidene)-2-(propylimino)-3-(o-tolyl)thiazolidin-4-one as determined by HPLC obtained when using a process according to Example 4 below.

Apart from a new process for the preparation of COMPOUND by using a new process for the preparation of (R)-3-chloro-4-(2,3-dihydroxypropoxy)-benzaldehyde, the present invention further also relates to (R)-3-chloro-4-(2,3-dihydroxypropoxy)-benzaldehyde as such.

DESCRIPTION OF THE FIGURE

FIG. 1 shows the X-ray powder diffraction diagram of (R)-3-chloro-4-(2,3-dihydroxypropoxy)-benzaldehyde in the crystalline form A, wherein the X-ray powder diffraction diagram is displayed against Cu Kα1 radiation. In the diagram the angle of refraction 2θ is plotted on the horizontal axis and the counts on the vertical axis. The X-ray diffraction diagram shows peaks having a relative intensity, as compared to the most intense peak in the diagram, of the following percentages (relative peak intensities given in parenthesis) at the indicated angles of refraction 2theta (peaks from the range 5-30° 2theta with relative intensity larger than 10% are reported): 7.3° (14%), 9.7° (34%), 12.7° (100%), 12.8° (46%), 13.3° (37%), 14.5° (29%), 14.7° (43%), 16.8° (17%), 19.4° (51%), 19.6° (64%), 20.5° (15%), 21.3° (11%), 21.5° (12%), 22.1° (50%), 22.7° (58%), 23.0° (42%), 23.3° (52%), 23.5° (18%), 24.1° (17%), 24.4° (38%), 25.9° (20%), 26.3° (46%), 26.5° (15%), 26.9° (13%), 27.7° (11%), 27.9° (44%), 28.5° (54%), and 29.7° (12%).

DETAILED DESCRIPTION OF THE INVENTION

In a first embodiment (embodiment i)), the present invention relates to a process for the preparation of (R)-3-chloro-4-(2,3-dihydroxypropoxy)-benzaldehyde (1):

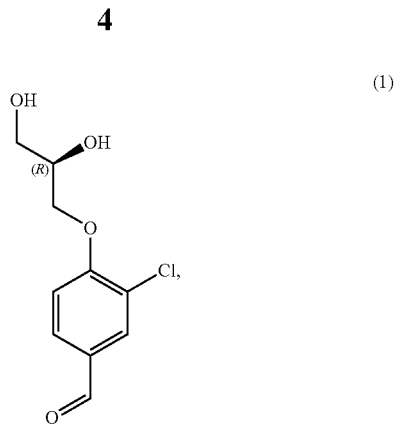

which process comprises reacting 3-chloro-4-hydroxybenzaldehyde with (R)-3-chloro-1,2-propanediol characterised in that the obtained (R)-3-chloro-4-(2,3-dihydroxypropoxy)-benzaldehyde is isolated by crystallisation.

The reaction of 3-chloro-4-hydroxybenzaldehyde with (R)-3-chloro-1,2-propanediol can be performed using standard methods for the alkylation of phenols, as described for example in March, J., Advanced Organic Chemistry: Reactions, Mechanism and Structure; 3rd edition; John Wiley & Sons: New York, 1985, 342-343. The alkylation reaction of embodiment i) preferably takes place in the solvent ethanol or n-propanol, such as especially n-propanol.

ii) In a further embodiment the present invention relates to the process according to embodiment i), wherein the reaction of 3-chloro-4-hydroxybenzaldehyde with (R)-3-chloro-1,2-propanediol is performed in the presence of the base potassium tert-butoxide and the solvent n-propanol, at elevated temperatures.

Preferably between 1.0 and 1.3 equivalents, such as especially 1.2 equivalents of potassium tert-butoxide and 1.0 equivalent of 3-chloro-4-hydroxybenzaldehyde are used. Most preferably 1.0 equivalent of 3-chloro-4-hydroxybenzaldehyde, 1.2 equivalents of potassium tert-butoxide and 1.3 equivalents of (R)-3-chloro-1,2-propanediol are used. Elevated temperatures means higher than 50° C., especially higher than 70° C., preferably between 50 and 100° C., such as especially between 70 and 100° C., and especially preferred about 95° C.

In a preferred embodiment the following order of addition is used: first n-propanol, second potassium tert-butoxide, third 3-chloro-4-hydroxybenzaldehyde and last (R)-3-chloro-1,2-propanediol.

iii) In a further embodiment the present invention relates to the process according to embodiment i) or ii), wherein the obtained (R)-3-chloro-4-(2,3-dihydroxypropoxy)-benzaldehyde (1) is crystallised in water plus a co-solvent.

Preferably the co-solvent is the solvent used for the reaction of 3-chloro-4-hydroxybenzaldehyde with (R)-3-chloro-1,2-propanediol.

Appropriate co-solvents are for example ethanol or n-propanol. Preferably the co-solvent is n-propanol. In a very preferred embodiment the ratio between water and n-propanol is 14:1 [v/v] and the concentration of (R)-3-chloro-4-(2,3-dihydroxypropoxy)-benzaldehyde in the crystallisation mixture is about 18 w %.

iv) In a further embodiment the present invention therefore also relates to the process according to embodiment iii), wherein the co-solvent is n-propanol, especially wherein the ratio between water and n-propanol is 14:1 [v/v] and the concentration of (R)-3-chloro-4-(2,3-dihydroxypropoxy)-benzaldehyde in the crystallisation mixture is about 18 w %.

v) In a further embodiment the present invention relates to the process according to any one of embodiments i) to iv), further comprising reacting the obtained (R)-3-chloro-4-(2,3-dihydroxypropoxy)-benzaldehyde (1) with 2-[(Z)-propylimino]-3-o-tolyl-thiazolidin-4-one to form (2Z,5Z)-5-(3-chloro-4-((R)-2,3-dihydroxypropoxy)benzylidene)-2-(propylimino)-3-(o-tolyl)thiazolidin-4-one (2):

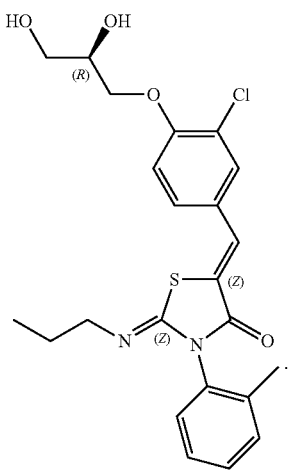

The reaction of (R)-3-chloro-4-(2,3-dihydroxypropoxy)-benzaldehyde (1) with 2-[(Z)-propylimino]-3-o-tolyl-thiazolidin-4-one can be performed under conditions which are typical for a Knoevenagel condensation. Such conditions are described in the literature for example in Jones, G., *Knoevenagel Condensation in Organic Reaction*, Wiley: New York, 1967, Vol. 15, p 204; or Prout, F. S., Abdel-Latif, A. A., Kamal, M. R., *J. Chem. Eng. Data*, 2012, 57, 1881-1886.

2-[(Z)-Propylimino]-3-o-tolyl-thiazolidin-4-one can be prepared as described in WO 2008/062376, preferably without the isolation and/or purification of intermediates such as the thiourea intermediate that occurs after reacting o-tolyl-iso-thiocyanate with n-propylamine. Preferably 2-[(Z)-propylimino]-3-o-tolyl-thiazolidin-4-one obtained according to WO 2008/062376 is also not isolated and/or purified before performing the Knoevenagel condensation, i.e. before reacting 2-[(Z)-propylimino]-3-o-tolyl-thiazolidin-4-one with (R)-3-chloro-4-(2,3-dihydroxypropoxy)-benzaldehyde (1), i.e. in a preferred embodiment compound (2) is prepared in a one-pot procedure analogous to that described in WO 2008/062376.

vi) In a further embodiment the present invention therefore also relates to the process according to embodiment v), wherein 2-[(Z)-propylimino]-3-o-tolyl-thiazolidin-4-one is prepared by reacting o-tolyl-iso-thiocyanate with n-propylamine followed by reaction with bromo-acetyl bromide and the base pyridine, wherein no isolation and/or purification of intermediates occurs and wherein the obtained 2-[(Z)-propylimino]-3-o-tolyl-thiazolidin-4-one is not isolated and/or purified before the reaction with (R)-3-chloro-4-(2,3-dihydroxypropoxy)-benzaldehyde (1), i.e. for example without any extractive aqueous work-up and concentration to dryness.

Preferably the following equivalents of o-tolyl-iso-thiocyanate, n-propylamine, bromo-acetyl bromide, and pyridine are used in the process according to embodiment vi): 1, 1-1.4, about 1, and about 2, respectively. Very preferably the following equivalents of o-tolyl-iso-thiocyanate, n-propylamine, bromo-acetyl bromide, and pyridine are used: 1.00, 1.02, 1.02, and 2.05, respectively. In another preferred embodiment the following equivalents of o-tolyl-iso-thiocyanate, n-propylamine, bromo-acetyl bromide, and pyridine are used: 1.00, 1.32, 1.10, and 2.05, respectively. Preferably the preparation of 2-[(Z)-propylimino]-3-o-tolyl-thiazolidin-4-one according to embodiment vi) takes place in the solvent dichloromethane.

In a process according to embodiment vi) the Knoevenagel condensation is preferably performed in the solvent ethanol, acetonitrile or acetic acid, preferably ethanol, and with sodium acetate, potassium acetate or pyridine as the base, such as especially sodium acetate or potassium acetate, preferably sodium acetate, especially between 1 and 3 equivalents, such as preferably about 2.3 equivalents, of sodium acetate. Preferably the Knoevenagel condensation is performed at elevated temperatures such as higher than 50° C., especially higher than 60° C., preferably between 50 and 85° C., such as especially between 60 and 85° C., and especially preferred at about 78° C.

In a preferred process according to embodiment vi) the preparation of 2-[(Z)-propylimino]-3-o-tolyl-thiazolidin-4-one takes place in the solvent dichloromethane whereby the dichloromethane is only partially removed before starting the Knoevenagel condensation.

vii) In a further embodiment the present invention therefore also relates to the process according to embodiment vi), wherein (R)-3-chloro-4-(2,3-dihydroxypropoxy)-benzaldehyde (1) is reacted with 2-[(Z)-propylimino]-3-o-tolyl-thiazolidin-4-one in the presence of the solvent ethanol and the base sodium acetate, at elevated temperatures.

viii) In a further embodiment the present invention relates to the process according to any one of embodiments v) to vii), characterised in that (R)-3-chloro-4-(2,3-dihydroxypropoxy)-benzaldehyde (1) is isolated by a single crystallisation before the reaction with 2-[(Z)-propylimino]-3-o-tolyl-thiazolidin-4-one.

ix) In a further embodiment the present invention relates to the process according to any one of embodiments v) to viii), wherein in a first isolation step the obtained compound (2) is isolated by crystallisation.

The crystallisation of the first isolation step can be performed in a mixture of acetonitrile and water or a mixture of ethanol and water, preferably in a mixture of ethanol and water.

x) In a further embodiment the present invention relates to the process according to embodiment ix), wherein the compound (2) obtained after the first isolation step is in the crystalline form characterised by the presence of peaks in the X-ray powder diffraction diagram at the following angles of refraction 2θ: 10.5°, 11.1°, 11.4°, 13.6°, 13.9°, 16.3°, 20.8°, 22.2°, 23.4°, 24.1°, 25.7°, 27.7°, 27.9°, 28.7°, and 29.3°, wherein the X-ray powder diffraction diagram is obtained by using Cu Kα1 radiation (λ=1.5406 Å) and stripping of the Kα2 component and wherein the accuracy of the 2θ values is in the range of +/−0.1-0.2°.

The crystalline form characterised by the presence of the peaks in the XRPD diagram according to embodiment x) is the crystalline form C of compound (2) as described in WO 2010/046835. The method used to determine the presence of the peaks at the indicated angles of refraction 2θ is that described on page 11, last paragraph, of WO 2010/046835.

xi) In a further embodiment the present invention relates to the process according to embodiment ix) or x), wherein the obtained crystalline compound (2) is further purified by one or more recrystallisation steps, preferably by a single recrystallisation step.

Such recrystallisation steps can be performed for example in ethanol.

xii) In a further embodiment the present invention relates to the compound (R)-3-chloro-4-(2,3-dihydroxypropoxy)-benzaldehyde.

xiii) In a further embodiment the present invention relates to the compound of embodiment xii) in crystalline form, such as especially an essentially pure crystalline form of the compound (R)-3-chloro-4-(2,3-dihydroxypropoxy)-benzaldehyde.

xiv) In a further embodiment the present invention relates to the crystalline form according to embodiment xiii), characterised by the presence of peaks in the X-ray powder diffraction diagram at the following angles of refraction 2θ: 7.3°, 9.7°, 12.7°, 13.3°, 19.6°, 22.1°, 27.9°, and 28.5°, wherein the X-ray powder diffraction diagram is obtained by using Cu Kα1 radiation (λ=1.5406 Å) and stripping of the Kα2 component and wherein the accuracy of the 2θ values is in the range of +/−0.1-0.2°.

xv) In a further embodiment the present invention relates to the crystalline form according to embodiment xiii) or xiv), which essentially shows the X-ray powder diffraction pattern as depicted in FIG. 1.

xvi) In a further embodiment the present invention relates to a crystalline form according to any one of embodiments xiii) to xv), which has a melting point of about 94° C. as determined by differential scanning calorimetry using the method as described herein.

xvii) In a further embodiment the present invention relates to a crystalline form of the compound (R)-3-chloro-4-(2,3-dihydroxypropoxy)-benzaldehyde obtainable by:
   i) adding potassium tert-butoxide (118 g, 1.20 eq.) to n-propanol (963 mL) followed by 3-chloro-4-hydroxybenzaldehyde (137 g, 1.00 eq.);
   ii) adding to the mixture (R)-3-chloro-1,2-propanediol (126 g, 1.30 eq.), heating the suspension to 90° C. and stirring it at this temperature for 17 h;
   iii) distilling off the solvent (500 mL) at 120° C. external temperature and reduced pressure;
   iv) adding water (1.1 L) and removing solvent (500 mL) by distillation;
   v) cooling the turbid solution to 20° C. and stirring for one hour to obtain a white suspension;
   vi) adding water (500 mL) and cooling the suspension to 10° C.;
   vii) filtering the suspension and washing the resulting filter cake with water (500 mL); and
   viii) drying the product at 50° C. and reduced pressure.

xviii) In a further embodiment the present invention relates to a crystalline form of the compound (R)-3-chloro-4-(2,3-dihydroxypropoxy)-benzaldehyde obtainable by:
   i) dissolving 10 mg of (R)-3-chloro-4-(2,3-dihydroxypropoxy)-benzaldehyde of at least 99.5% purity by 1H-NMR assay in a 4 mL vial by adding 1 mL of pure ethanol (puriss p.a.); and
   ii) allowing the solvent to evaporate through a small hole in the cap (2 mm of diameter) of the vial until complete dryness.

xix) In a further embodiment the present invention relates to the crystalline form according to embodiment xvii) or xviii), which has a melting point of about 94° C. as determined by differential scanning calorimetry using the method as described herein.

xx) In a further embodiment the present invention relates to the crystalline form according to any one of embodiments xiii) to xvi), obtainable by the process of embodiment xvii) or xviii).

xxi) In a further embodiment the present invention relates to a process for the preparation of (2Z,5Z)-5-(3-chloro-4-((R)-2,3-dihydroxypropoxy)benzylidene)-2-(propylimino)-3-(o-tolyl)thiazolidin-4-one comprising the process according to any one of embodiments i) to xi).

xxii) In a further embodiment the present invention relates to the use of the compound of any one of embodiments xii) to xx) for the preparation of (2Z,5Z)-5-(3-chloro-4-((R)-2,3-dihydroxypropoxy)benzylidene)-2-(propylimino)-3-(o-tolyl)thiazolidin-4-one.

Based on the dependencies of the different embodiments i) to xix) as disclosed hereinabove, the following embodiments are thus possible and intended and herewith specifically disclosed in individualized form:
i), ii)+i), iii)+i), iii)+ii)+i), iv)+iii)+i), iv)+iii)+ii)+i), v)+i), v)+ii)+i), v)+iii)+i), v)+iii)+ii)+i), v)+iv)+iii)+i), v)+iv)+iii)+ii)+i), vi)+v)+i), vi)+v)+ii)+i), vi)+v)+iii)+i), vi)+v)+iii)+ii)+i), vi)+v)+iv)+iii)+i), vi)+v)+iv)+iii)+ii)+i), vii)+vi)+v)+i), vii)+vi)+v)+ii)+i), vii)+vi)+v)+iii)+i), vii)+vi)+v)+iii)+ii)+i), vii)+vi)+v)+iv)+iii)+i), vii)+vi)+v)+iv)+iii)+ii)+i), viii)+v)+i), viii)+v)+ii)+i), viii)+v)+iii)+i), viii)+v)+iii)+ii)+i), viii)+v)+iv)+iii)+i), viii)+v)+iv)+iii)+ii)+i), viii)+vi)+v)+i), viii)+vi)+v)+ii)+i), viii)+vi)+v)+iii)+i), viii)+vi)+v)+iii)+ii)+i), viii)+vi)+v)+iv)+iii)+i), viii)+vi)+v)+iv)+iii)+ii)+i), viii)+vii)+vi)+v)+i), viii)+vii)+vi)+v)+ii)+i), viii)+vii)+vi)+v)+iii)+i), viii)+vii)+vi)+v)+iii)+ii)+i), viii)+vii)+vi)+v)+iv)+iii)+i), viii)+vii)+vi)+v)+iv)+iii)+ii)+i), ix)+v)+i), ix)+v)+ii)+i), ix)+v)+iii)+i), ix)+v)+iii)+ii)+i), ix)+v)+iv)+iii)+i), ix)+v)+iv)+iii)+ii)+i), ix)+vi)+v)+i), ix)+vi)+v)+ii)+i), ix)+vi)+v)+iii)+i), ix)+vi)+v)+iii)+ii)+i), ix)+vi)+v)+iv)+iii)+i), ix)+vi)+v)+iv)+iii)+ii)+i), ix)+vii)+vi)+v)+i), ix)+vii)+vi)+v)+ii)+i), ix)+vii)+vi)+v)+iii)+i), ix)+vii)+vi)+v)+iii)+ii)+i), ix)+vii)+vi)+v)+iv)+iii)+i), ix)+vii)+vi)+v)+iv)+iii)+ii)+i), ix)+viii)+v)+i), ix)+viii)+v)+ii)+i), ix)+viii)+v)+iii)+i), ix)+viii)+v)+iii)+ii)+i), ix)+viii)+v)+iv)+iii)+i), ix)+viii)+v)+iv)+iii)+ii)+i), ix)+viii)+vi)+v)+i), ix)+viii)+vi)+v)+ii)+i), ix)+viii)+vi)+v)+iii)+i), ix)+viii)+vi)+v)+iii)+ii)+i), ix)+viii)+vi)+v)+iv)+iii)+i), ix)+viii)+vi)+v)+iv)+iii)+ii)+i), ix)+viii)+vii)+vi)+v)+i), ix)+viii)+vii)+vi)+v)+ii)+i), ix)+viii)+vii)+vi)+v)+iii)+i), ix)+viii)+vii)+vi)+v)+iii)+ii)+i), ix)+viii)+vii)+vi)+v)+iv)+iii)+i), ix)+viii)+vii)+vi)+v)+iv)+iii)+ii)+i), x)+ix)+v)+i), x)+ix)+v)+ii)+i), x)+ix)+v)+iii)+i), x)+ix)+v)+iii)+ii)+i), x)+ix)+v)+iv)+iii)+i), x)+ix)+v)+iv)+iii)+ii)+i), x)+ix)+vi)+v)+i), x)+ix)+vi)+v)+ii)+i), x)+ix)+vi)+v)+iii)+i), x)+ix)+vi)+v)+iii)+ii)+i), x)+ix)+vi)+v)+iv)+iii)+i), x)+ix)+vi)+v)+iv)+iii)+ii)+i), x)+ix)+vii)+vi)+v)+i), x)+ix)+vii)+vi)+v)+ii)+i), x)+ix)+vii)+vi)+v)+iii)+i), x)+ix)+vii)+vi)+v)+iii)+ii)+i), x)+ix)+vii)+vi)+v)+iv)+iii)+i), x)+ix)+vii)+vi)+v)+iv)+iii)+ii)+i), x)+ix)+viii)+v)+i), x)+ix)+viii)+v)+ii)+i), x)+ix)+viii)+v)+iii)+i), x)+ix)+viii)+v)+iii)+ii)+i), x)+ix)+viii)+v)+iv)+iii)+i), x)+ix)+viii)+v)+iv)+iii)+ii)+i), x)+ix)+viii)+vi)+v)+i), x)+ix)+viii)+vi)+v)+ii)+i), x)+ix)+viii)+vi)+v)+iii)+i), x)+ix)+viii)+vi)+v)+iii)+ii)+i), x)+ix)+viii)+vi)+v)+iv)+iii)+i), x)+ix)+viii)+vi)+v)+iv)+iii)+ii)+i), x)+ix)+viii)+vii)+vi)+v)+i), x)+ix)+viii)+vii)+vi)+v)+ii)+i), x)+ix)+viii)+vii)+vi)+v)+iii)+i), x)+ix)+viii)+vii)+vi)+v)+iii)+ii)+i), x)+ix)+viii)+vii)+vi)+v)+iv)+iii)+i), x)+ix)+viii)+vii)+vi)+v)+iv)+iii)+ii)+i), xi)+ix)+v)+i), xi)+ix)+v)+ii)+i), xi)+ix)+v)+iii)+i), xi)+ix)+v)+iii)+ii)+i), xi)+ix)+v)+iv)+iii)+i), xi)+ix)+v)+iv)+iii)+ii)+i), xi)+ix)+vi)+v)+i), xi)+ix)+vi)+v)+ii)+i), xi)+ix)+vi)+v)+iii)+i), xi)+ix)+vi)+v)+iii)+ii)+i), xi)+ix)+vi)+v)+iv)+iii)+i), xi)+ix)+vi)+v)+iv)+iii)+ii)+i), xi)+ix)+vii)+vi)+v)+i), xi)+ix)+vii)+vi)+v)+ii)+i), xi)+ix)+vii)+vi)+v)+iii)+i), xi)+ix)+vii)+vi)+v)+iii)+ii)+i), xi)+ix)+vii)+vi)+v)+iv)+iii)+i), xi)+ix)+vii)+vi)+v)+iv)+iii)+ii)+i), xi)+ix)+viii)+v)+i), xi)+ix)+viii)+v)+ii)+i), xi)+ix)+viii)+v)+iii)+i), xi)+ix)+viii)+v)+iii)+ii)+i), xi)+ix)+viii)+v)+iv)+iii)+i), xi)+ix)+viii)+v)+iv)+iii)+ii)+i), xi)+ix)+viii)+vi)+v)+i), xi)+ix)+viii)+vi)+v)+ii)+i), xi)+ix)+viii)+vi)+v)+iii)+i), xi)+ix)+viii)+vi)+v)+iii)+ii)+i), xi)+ix)+viii)+vi)+v)+iv)+iii)+i), xi)+ix)+viii)+vi)+v)+iv)+iii)+ii)+i), xi)+ix)+viii)+vii)+vi)+v)+i), xi)+ix)+viii)+vii)+vi)+v)+ii)+i), xi)+ix)+viii)+vii)+vi)+v)+iii)+i), xi)+ix)+viii)+vii)+vi)+v)+iii)+ii)+i), xi)+ix)+viii)+vii)+vi)+v)+iv)+iii)+i), xi)+ix)+viii)+vii)+vi)+v)+iv)+iii)+ii)+i), xi)+x)+ix)+v)+i), xi)+x)+ix)+v)+ii)+i), xi)+x)+ix)+v)+iii)+i), xi)+x)+ix)+v)+iii)+ii)+i), xi)+x)+ix)+v)+iv)+iii)+i), xi)+x)+ix)+v)+iv)+iii)+ii)+i), xi)+x)+ix)+vi)+v)+i), xi)+x)+ix)+vi)+v)+ii)+i), xi)+x)+ix)+vi)+v)+iii)+i), xi)+x)+ix)+vi)+v)+iii)+ii)+i), xi)+x)+ix)+vi)+v)+iv)+iii)+i), xi)+x)+ix)+vi)+v)+iv)+iii)+ii)+i), xi)+x)+ix)+vii)+vi)+v)+i), xi)+x)+ix)+vii)+vi)+v)+ii)+i), xi)+x)+ix)+vii)+vi)+v)+iii)+i), xi)+x)+ix)+vii)+vi)+v)+iii)+ii)+i), xi)+x)+ix)+vii)+vi)+v)+iv)+iii)+i), xi)+x)+ix)+vii)+vi)+v)+iv)+iii)+ii)+i), xi)+x)+ix)+viii)+v)+i), xi)+x)+ix)+viii)+v)+ii)+i), xi)+x)+ix)+viii)+v)+iii)+i), xi)+x)+ix)+viii)+v)+iii)+ii)+i), xi)+x)+ix)+viii)+v)+iv)+iii)+i), xi)+x)+ix)+viii)+v)+iv)+iii)+ii)+i), xi)+x)+ix)+viii)+vi)+v)+i), xi)+x)+ix)+viii)+vi)+v)+ii)+i), xi)+x)+ix)+viii)+vi)+v)+iii)+i), xi)+x)+ix)+viii)+vi)+v)+iii)+ii)+i), xi)+x)+ix)+viii)+vi)+v)+iv)+iii)+i), xi)+x)+ix)+viii)+vi)+v)+iv)+iii)+ii)+i), xi)+x)+ix)+viii)+vii)+vi)+v)+i), xi)+x)+ix)+viii)+vii)+vi)+v)+ii)+i), xi)+x)+ix)+viii)+vii)+vi)+v)+iii)+i), xi)+x)+ix)+viii)+vii)+vi)+v)+iii)+ii)+i), xi)+x)+ix)+viii)+vii)+vi)+v)+iv)+iii)+i), xi)+x)+ix)+viii)+vii)+vi)+v)+iv)+iii)+ii)+i), xii), xiii)+xii), xiv)+xiii)+xii), xv)+xiii)+xii), xv)+xiv)+xiii)+xii), xvi)+xiii)+xii), xvi)+xiv)+xiii)+xii), xvi)+xv)+xiii)+xii), xvi)+xv)+xiv)+xiii)+xii), xvii), xviii), xix)+xvii), and xix)+xviii).

In the list above the numbers refer to the embodiments according to their numbering provided hereinabove whereas "+" indicates the dependency from another embodiment. The different individualized embodiments are separated by commas. In other words, "iii)+ii)+i)" for example refers to embodiment iii) depending on embodiment ii) depending on embodiment i), i.e. embodiment "iii)+ii)+i)" corresponds to embodiment i) further limited by the features of embodiments ii) and iii). Using the same nomenclature, the present invention further also relates to the following individualized embodiments based on the dependencies of embodiment xx): xiii)+xii) obtainable by xvii), xiv)+xiii)+xii) obtainable by xvii), xv)+xiii)+xii) obtainable by xvii), xv)+xiv)+xiii)+xii) obtainable by xvii), xvi)+xiii)+xii) obtainable by xvii), xvi)+xiv)+xiii)+xii) obtainable by xvii), xvi)+xv)+xiii)+xii) obtainable by xvii), xvi)+xv)+xiv)+xiii)+xii) obtainable by xvii), xiii)+xii) obtainable by xviii), xiv)+xiii)+xii) obtainable by xviii), xv)+xiii)+xii) obtainable by xviii), xv)+xiv)+xiii)+xii) obtainable by xviii), xvi)+xiii)+xii) obtainable by xviii), xvi)+xiv)+xiii)+xii) obtainable by xviii), xvi)+xv)+xiii)+xii) obtainable by xviii), and xvi)+xv)+xiv)+xiii)+xii) obtainable by xviii). Likewise the present invention further also relates to the following individualized embodiments based on the embodiment xxi): xxi) comprising i), xxi) comprising ii)+i), xxi) comprising iii)+i), xxi) comprising iii)+ii)+i), xxi) comprising iv)+iii)+i), xxi) comprising iv)+iii)+ii)+i), xxi) comprising v)+i), xxi) comprising v)+ii)+i), xxi) comprising v)+iii)+i), xxi) comprising v)+iii)+ii)+i), xxi) comprising v)+iv)+iii)+i), xxi) comprising v)+iv)+iii)+ii)+i), xxi) comprising vi)+v)+i), xxi) comprising vi)+v)+ii)+i), xxi) comprising vi)+v)+iii)+i), xxi) comprising vi)+v)+iii)+ii)+i), xxi) comprising vi)+v)+iv)+iii)+i), xxi) comprising vi)+v)+iv)+iii)+ii)+i), xxi) comprising vii)+vi)+v)+i), xxi) comprising vii)+v)+ii)+i), xxi) comprising vii)+vi)+v)+iii)+i), xxi) comprising vii)+vi)+v)+iii)+ii)+i), xxi) comprising vii)+vi)+v)+iv)+iii)+i), xxi) comprising vii)+vi)+v)+iv)+iii)+ii)+i), xxi) comprising viii)+v)+i), xxi) comprising viii)+v)+ii)+i), xxi) comprising viii)+v)+iii)+i), xxi) comprising viii)+v)+iii)+ii)+i), xxi) comprising viii)+v)+iv)+iii)+i), xxi) comprising viii)+v)+iv)+iii)+ii)+i), xxi) comprising viii)+vi)+v)+i), xxi) comprising viii)+vi)+v)+ii)+i), xxi) comprising viii)+vi)+v)+iii)+i), xxi) comprising viii)+vi)+v)+iii)+ii)+i), xxi) comprising viii)+vi)+v)+iv)+iii)+i), xxi) comprising viii)+vi)+v)+iv)+iii)+ii)+i), xxi) comprising viii)+vii)+vi)+v)+i), xxi) comprising viii)+vii)+vi)+v)+ii)+i), xxi) comprising viii)+vii)+vi)+v)+iii)+i), xxi) comprising viii)+vii)+vi)+v)+iii)+ii)+i), xxi) comprising viii)+vii)+vi)+v)+iv)+iii)+i), xxi) comprising viii)+vii)+vi)+v)+iv)+iii)+ii)+i), xxi) comprising ix)+v)+i), xxi) comprising ix)+v)+ii)+i), xxi) comprising ix)+v)+iii)+i), xxi) comprising ix)+v)+iii)+ii)+i), xxi) comprising ix)+v)+iv)+iii)+i), xxi) comprising ix)+v)+iv)+iii)+ii)+i), xxi) comprising ix)+vi)+v)+i), xxi) comprising ix)+vi)+v)+ii)+i), xxi) comprising ix)+vi)+v)+iii)+i), xxi) comprising ix)+vi)+v)+iii)+ii)+i), xxi) comprising ix)+vi)+v)+iv)+iii)+i), xxi) comprising ix)+vi)+v)+iv)+iii)+ii)+i), xxi) comprising ix)+vii)+vi)+v)+i), xxi) comprising ix)+vii)+vi)+v)+ii)+i), xxi) comprising ix)+vii)+vi)+v)+iii)+i), xxi) comprising ix)+vii)+vi)+v)+iii)+ii)+i), xxi) comprising ix)+vii)+vi)+v)+iv)+iii)+i), xxi) comprising ix)+vii)+vi)+v)+iv)+iii)+ii)+i), xxi) comprising ix)+viii)+v)+i), xxi) comprising ix)+viii)+v)+ii)+i), xxi) comprising ix)+viii)+v)+iii)+i), xxi) comprising ix)+viii)+v)+iii)+ii)+i), xxi) comprising ix)+viii)+v)+iv)+iii)+i), xxi) comprising ix)+viii)+v)+iv)+iii)+ii)+i), xxi) comprising ix)+viii)+vi)+v)+i), xxi) comprising ix)+viii)+vi)+v)+ii)+i), xxi) comprising ix)+viii)+vi)+v)+iii)+i), xxi) comprising ix)+viii)+vi)+v)+iii)+ii)+i), xxi) comprising ix)+viii)+vi)+v)+iv)+iii)+i), xxi) comprising ix)+viii)+vi)+v)+iv)+iii)+ii)+i), xxi) comprising ix)+viii)+vii)+vi)+v)+i), xxi) comprising ix)+viii)+vii)+vi)+v)+ii)+i), xxi) comprising ix)+viii)+vii)+vi)+v)+iii)+i), xxi) comprising ix)+viii)+vii)+vi)+v)+iii)+ii)+i), xxi) comprising ix)+viii)+vii)+vi)+v)+iv)+iii)+i), xxi) comprising ix)+viii)+vii)+vi)+v)+iv)+iii)+ii)+i), xxi) comprising x)+ix)+v)+i), xxi) comprising x)+ix)+v)+ii)+i), xxi) comprising x)+ix)+v)+iii)+i), xxi) comprising x)+ix)+v)+iii)+ii)+i), xxi) comprising x)+ix)+v)+iv)+iii)+i), xxi) comprising x)+ix)+v)+iv)+iii)+ii)+i), xxi) comprising x)+ix)+vi)+v)+i), xxi) comprising x)+ix)+vi)+v)+ii)+i), xxi) comprising x)+ix)+vi)+v)+iii)+i), xxi) comprising x)+ix)+vi)+v)+iii)+ii)+i), xxi) comprising x)+ix)+vi)+v)+iv)+iii)+i), xxi) comprising x)+ix)+vi)+v)+iv)+iii)+ii)+i), xxi) comprising x)+ix)+vii)+vi)+v)+i), xxi) comprising x)+ix)+vii)+vi)+v)+ii)+i), xxi) comprising x)+ix)+vii)+vi)+v)+iii)+i), xxi) comprising x)+ix)+vii)+vi)+v)+iii)+ii)+i), xxi) comprising x)+ix)+vii)+vi)+v)+iv)+iii)+i), xxi) comprising x)+ix)+vii)+vi)+v)+iv)+iii)+ii)+i), xxi) comprising x)+ix)+viii)+v)+i), xxi) comprising x)+ix)+viii)+v)+ii)+i), xxi) comprising x)+ix)+viii)+v)+iii)+i), xxi) comprising x)+ix)+viii)+v)+iii)+ii)+i), xxi) comprising x)+ix)+viii)+v)+iv)+iii)+i), xxi) comprising x)+ix)+viii)+v)+iv)+iii)+ii)+i), xxi) comprising x)+ix)+viii)+vi)+v)+i), xxi) comprising x)+ix)+viii)+vi)+v)+ii)+i), xxi) comprising x)+ix)+viii)+vi)+v)+iii)+i), xxi) comprising x)+ix)+viii)+vi)+v)+iii)+ii)+i), xxi) comprising x)+ix)+viii)+vi)+v)+iv)+iii)+i), xxi) comprising x)+ix)+viii)+vi)+v)+iv)+iii)+ii)+i), xxi) comprising x)+ix)+viii)+vii)+vi)+v)+i), xxi) comprising x)+ix)+viii)+vii)+vi)+v)+ii)+i), xxi) comprising x)+ix)+viii)+vii)+vi)+v)+iii)+i), xxi) comprising x)+ix)+viii)+vii)+vi)+v)+iii)+ii)+i), xxi) comprising x)+ix)+viii)+vii)+vi)+v)+iv)+iii)+i), xxi) comprising x)+ix)+viii)+vii)+vi)+v)+iv)+iii)+ii)+i), xxi) comprising xi)+ix)+v)+i), xxi) comprising xi)+ix)+v)+ii)+i), xxi) comprising xi)+ix)+v)+iii)+i), xxi) comprising xi)+ix)+v)+iii)+ii)+i), xxi) comprising xi)+ix)+v)+iv)+iii)+i), xxi) comprising xi)+ix)+v)+iv)+iii)+ii)+i), xxi) comprising xi)+ix)+vi)+v)+i), xxi) comprising xi)+ix)+vi)+v)+ii)+i), xxi) comprising xi)+ix)+vi)+v)+iii)+i), xxi) comprising xi)+ix)+vi)+v)+iii)+ii)+i), xxi) comprising xi)+ix)+vi)+v)+iv)+iii)+i), xxi) comprising xi)+ix)+vi)+v)+iv)+iii)+ii)+i), xxi) comprising xi)+ix)+vii)+vi)+v)+i), xxi) comprising xi)+ix)+vii)+vi)+v)+ii)+i), xxi) comprising xi)+ix)+vii)+vi)+v)+iii)+i), xxi) comprising xi)+ix)+vii)+vi)+v)+iii)+ii)+i), xxi) comprising xi)+ix)+vii)+vi)+v)+iv)+iii)+i), xxi) comprising xi)+ix)+vii)+vi)+v)+iv)+iii)+ii)+i), xxi) comprising xi)+ix)+viii)+v)+i), xxi) comprising xi)+ix)+viii)+v)+ii)+i), xxi) comprising xi)+ix)+viii)+v)+iii)+i), xxi) comprising xi)+ix)+viii)+v)+iii)+ii)+i), xxi) comprising xi)+ix)+viii)+v)+iv)+iii)+i), xxi) comprising xi)+ix)+viii)+v)+iv)+iii)+ii)+i), xxi) comprising xi)+ix)+viii)+vi)+v)+i), xxi) comprising xi)+ix)+viii)+vi)+v)+ii)+i), xxi) comprising xi)+ix)+viii)+vi)+v)+iii)+i), xxi) comprising xi)+ix)+viii)+vi)+v)+iii)+ii)+i), xxi) comprising xi)+ix)+viii)+vi)+v)+iv)+iii)+i), xxi) comprising xi)+ix)+viii)+vi)+v)+iv)+iii)+ii)+i), xxi) comprising xi)+ix)+viii)+vii)+vi)+v)+i), xxi) comprising xi)+ix)+viii)+vii)+vi)+v)+ii)+i), xxi) comprising xi)+ix)+viii)+vii)+vi)+v)+iii)+i), xxi) comprising xi)+ix)+viii)+vii)+vi)+v)+iii)+ii)+i), xxi) comprising xi)+ix)+viii)+vii)+vi)+v)+iv)+iii)+i), xxi) comprising xi)+ix)+viii)+vii)+vi)+v)+iv)+iii)+ii)+i), xxi) comprising xi)+x)+ix)+v)+i), xxi) comprising xi)+x)+ix)+v)+ii)+i), xxi) comprising xi)+x)+ix)+v)+iii)+i), xxi) comprising xi)+x)+ix)+v)+iii)+ii)+i), xxi) comprising xi)+x)+ix)+v)+iv)+iii)+i), xxi) comprising xi)+x)+ix)+v)+iv)+iii)+ii)+i), xxi) comprising xi)+x)+ix)+vi)+v)+i), xxi) comprising xi)+x)+ix)+vi)+v)+ii)+i), xxi) comprising xi)+x)+ix)+vi)+v)+iii)+i), xxi) comprising xi)+x)+ix)+vi)+v)+iii)+ii)+i), xxi) comprising xi)+x)+ix)+vi)+v)+iv)+iii)+i), xxi) comprising xi)+x)+ix)+vi)+v)+iv)+iii)+ii)+i), xxi) comprising xi)+x)+ix)+vii)+vi)+v)+i), xxi) comprising xi)+x)+ix)+vii)+vi)+v)+ii)+i), xxi) comprising xi)+x)+ix)+vii)+vi)+v)+iii)+i), xxi) comprising xi)+x)+ix)+vii)+vi)+v)+iii)+ii)+i), xxi) comprising xi)+x)+ix)+vii)+vi)+v)+iv)+iii)+i), xxi) comprising xi)+x)+ix)+vii)+vi)+v)+iv)+iii)+ii)+i), xxi) comprising xi)+x)+ix)+viii)+v)+i), xxi) comprising xi)+x)+ix)+viii)+v)+ii)+i), xxi) comprising xi)+x)+ix)+viii)+v)+iii)+i), xxi) comprising xi)+x)+ix)+viii)+v)+iii)+ii)+i), xxi) comprising xi)+x)+ix)+viii)+v)+iv)+iii)+i), xxi) comprising xi)+x)+ix)+viii)+v)+iv)+iii)+ii)+i), xxi) comprising xi)+x)+ix)+viii)+vi)+v)+i), xxi) comprising xi)+x)+ix)+viii)+vi)+v)+ii)+i), xxi) comprising xi)+x)+ix)+viii)+vi)+v)+iii)+i), xxi) comprising xi)+x)+ix)+viii)+vi)+v)+iii)+ii)+i), xxi) comprising xi)+x)+ix)+viii)+vi)+v)+iv)+iii)+i), xxi) comprising xi)+x)+ix)+viii)+vi)+v)+iv)+iii)+ii)+i), xxi) comprising xi)+x)+ix)+viii)+vii)+vi)+v)+i), xxi) comprising xi)+x)+ix)+viii)+vii)+vi)+v)+ii)+i), xxi) comprising xi)+x)+ix)+viii)+vii)+vi)+v)+iii)+i), xxi) comprising xi)+x)+ix)+viii)+vii)+vi)+v)+iii)+ii)+i), xxi) comprising xi)+x)+ix)+viii)+vii)+vi)+v)+iv)+iii)+i), and xxi) comprising xi)+x)+ix)+viii)+vii)+vi)+v)+iv)+iii)+ii)+i). Likewise the present invention further also relates to the following individualized embodiments based on the embodiment xxii): xxii) using xii), xxii) using xiii)+xii), xxii) using xiv)+xiii)+xii), xxii) using xv)+xiii)+xii), xxii) using xv)+xiv)+xiii)+xii), xxii) using xvi)+xiii)+xii), xxii) using xvi)+xiv)+xiii)+xii), xxii) using xvi)+xv)+xiii)+xii), xxii) using xvi)+xv)+xiv)+xiii)+xii), xxii) using xvii), xxii) using xviii), xxii) using xix)+xvii), xxii) using xix)+xviii), xxii) using xiii)+xii) obtainable by xvii), xxii) using xiv)+xiii)+xii) obtainable by xvii), xxii) using xv)+xiii)+xii) obtainable by xvii), xxii) using xv)+xiv)+xiii)+xii) obtainable by xvii), xxii) using xvi)+xiii)+xii) obtainable by xvii), xxii) using xvi)+xiv)+xiii)+xii) obtainable by xvii), xxii) using xvi)+xv)+xiii)+xii) obtainable by xvii), xxii) using xvi)+xv)+xiv)+xiii)+xii) obtainable by xvii), xxii) using xiii)+xii) obtainable by xviii), xxii) using xiv)+xiii)+xii) obtainable by xviii), xxii) using xv)+xiii)+xii) obtainable by xviii), xxii) using xv)+xiv)+xiii)+xii) obtainable by xviii), xxii) using xvi)+xiii)+xii) obtainable by xviii), xxii) using xvi)+xiv)+xiii)+xii) obtainable by xviii), xxii) using xvi)+xv)+xiii)+xii) obtainable by xviii), and xxii) using xvi)+xv)+xiv)+xiii)+xii) obtainable by xviii).

The term "essentially pure" is understood in the context of the present invention to mean especially that at least 90, preferably at least 95, and most preferably at least 99 percent by weight of the crystals of (R)-3-chloro-4-(2,3-dihydroxypropoxy)-benzaldehyde are present in a single crystalline form, such as especially the crystalline form A of (R)-3-chloro-4-(2,3-dihydroxypropoxy)-benzaldehyde as described herein.

When defining the presence of a peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 1, the term "essentially" means that at least the major peaks of the diagram depicted in said FIGURE, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the present application to an interval extending from X minus 10% of X to X plus 10% of X, and preferably to an interval extending from X minus 5% of X to X plus 5% of X. In the particular case of temperatures, the term "about" placed before a temperature "Y" refers in the present application to an interval extending from the temperature Y minus 5° C. to Y plus 5° C., and preferably to an interval extending from Y minus 3° C. to Y plus 3° C.

When specifying an angle of diffraction 2theta (2θ) for a peak in the present application, it should be understood that the value given is to be understood as an interval from said value minus 0.2° to said value plus 0.2°, and preferably from said value minus 0.1° to said value plus 0.1°.

EXAMPLES

The following examples illustrate the invention.
Methods Used:
X-Ray Powder Diffraction Analysis:

X-ray powder diffraction patterns for crystalline form A of (R)-3-chloro-4-(2,3-dihydroxypropoxy)-benzaldehyde were collected on a Bruker D8 Advance powder X-ray diffractometer equipped with a LynxEye detector using $Cu_{K\alpha}$ radiation in reflection (Bragg-Brentano) geometry. The X-ray tube was run at 40 kV/40 mA. Divergence slit and antiscatter slit were both set at 0.3. The step size was 0.02° 2θ with a step time of 0.9 seconds and a scanning range of 2-50° in 2θ was applied. The powder was slightly pressed into a silicon single crystal sample holder with 0.5 mm depth and a cavity diameter of 20 mm. The samples were rotated in their own plane during the measurement. Diffraction data are reported using Cu Kα1 (wavelength λ=1.5406 Å), after the Kα2 (wavelength λ=1.5444 Å) component has been stripped using the instrument evaluation software (Diffrac.EVA v1.3). The accuracy of the 2θ values as provided herein is in the range of +/−0.1-0.2° as it is generally the case for conventionally recorded X-ray powder diffraction patterns.

Differential Scanning Calorimetry:

DSC data for crystalline form A of (R)-3-chloro-4-(2,3-dihydroxypropoxy)-benzaldehyde were collected on a Mettler Toledo STAR System DSC822e module and evaluated with STAR software version 9.2. The instrument was calibrated for energy and temperature using certified indium. Typically 2-3 mg of a sample is placed in a standard 40 microliter aluminium pan that is automatically pierced prior to measurement. Measuring conditions are 10° C. min$^{-1}$ in the range of minus 20 to 320° C. Peak temperatures are reported.

ABBREVIATIONS

As Used Herein approx. approximately
DSC differential scanning calorimetry
eq. equivalent(s)
Fig. figure
h hour(s)
HPLC high performance liquid chromatography
IPC in-process control
min minute(s)
NMR nuclear magnetic resonance
v/v volume per volume
w % weight percent
w/w weight per weight
XRPD X-ray powder diffraction Example 1

(2Z,5Z)-5-(3-Chloro-4-((R)-2,3-dihydroxypropoxy) benzylidene)-2-(propylimino)-3-(o-tolyl)thiazolidin-4-one

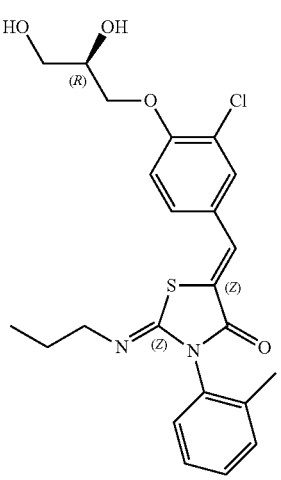

a) Preparation of (2Z,5Z)-5-(3-chloro-4-hydroxy-benzylidene)-2-propylimino-3-o-tolyl-thiazolidin-4-one

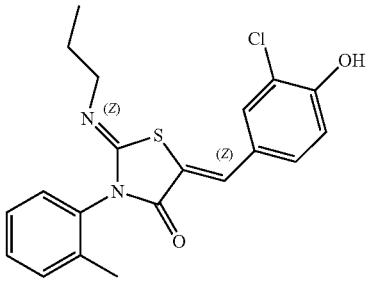 [SMILES: CCC/N=C1\S/C(=C\c2ccc(O)c(Cl)c2)C(=O)N1c1ccccc1C]

Acetic acid solution: To acetic acid (149.2 mL) are added sodium acetate (11.11 g, 2.00 eq.) and 3-chloro-4-hydroxy-benzaldehyde (10.60 g, 1.00 eq.) at 20° C. The mixture is stirred at 20° C. until complete dissolution (2 to 3 h).

n-Propylamine (4.04 g, 1.00 eq.) is added to a solution of o-tolyl-iso-thiocyanate (10 g, 1.00 eq.) in dichloromethane (100 mL) at 20° C. The resulting pale yellow solution is agitated for 40 min at 20° C. before IPC (conversion specification ≥99.0%). The reaction is cooled to −2° C. Bromoacetyl bromide (13.53 g, 1.00 eq.) is added and the resulting solution is stirred for 15 min at −2° C. Pyridine (10.92 g, 2.05 eq.) is then added slowly at −2° C. The intensive yellow reaction mixture is stirred for 15 min at −2° C. before IPC (conversion specification 93.0%). 70 mL of dichloromethane are distilled off under atmospheric pressure and jacket temperature of 60° C. The temperature is adjusted to 42° C. and the acetic acid solution is added to the reaction mixture. The resulting solution is heated to 58° C. and stirred at this temperature for 15 h before IPC (conversion specification ≥95%). 25 mL of solvents are distilled off under vacuum 900-500 mbars and jacket temperature of 80° C. The temperature is adjusted to 60° C. and water (80.1 mL) is added to the reaction mixture over 1 h. The resulting yellow suspension is stirred at 60° C. for 30 min. The suspension is cooled to 20° C. over 1 h and stirred at this temperature for 30 min.

The product is filtered and washed with a mixture of acetic acid (30 mL) and water (16 mL) and with water (50 mL) at 20° C. The product is dried under vacuum at 50° C. for 40 h to afford a pale yellow solid; yield 25.93 g (78%).

b) Preparation of crude (2Z,5Z)-5-(3-chloro-4-((R)-2,3-dihydroxypropoxy)benzylidene)-2-(propylimino)-3-(o-tolyl)thiazolidin-4-one To a suspension of (2Z,5Z)-5-(3-chloro-4-hydroxy-benzylidene)-2-propylimino-3-o-tolyl-thiazolidin-4-one (10.00 g, 1.00 eq.) in ethanol (47.2 mL) is added (R)-3-chloro-1,2-propanediol (3.37 g, 1.18 eq.) at 20° C. Potassium tert-butoxide (3.39 g, 1.13 eq.) is added in portions at 20° C. The resulting fine suspension is stirred at 20° C. for 25 min before being heated to reflux (88° C.). The reaction mixture is stirred at this temperature for 24 h before IPC (conversion specification ≥96.0%). After cooling down to 60° C., acetonitrile (28.6 mL) and water (74.9 mL) are added. The resulting clear solution is cooled from 60° C. to 0° C. over 2 h. During the cooling ramp, (2Z,5Z)-5-(3-chloro-4-((R)-2,3-dihydroxypropoxy)benzylidene)-2-(propylimino)-3-(o-tolyl)thiazolidin-4-one seeds of crystalline form C (0.010 g, 0.001 eq.; crystalline form C can be prepared as described in WO 2010/

046835) are added at 50° C. The suspension is heated from 0° C. to 50° C., cooled to 0° C. over 6 h and stirred at this temperature for 12 h.

The product is filtered and washed with a mixture of acetonitrile (23.4 mL) and water (23.4 mL) at 0° C. The product is dried under vacuum at 45° C. for 24 h to afford a pale yellow solid; yield 11.91 g (84%).

c) Purification of (2Z,5Z)-5-(3-chloro-4-((R)-2,3-dihydroxypropoxy)benzylidene)-2-(propylimino)-3-(o-tolyl)thiazolidin-4-one Recrystallisation I: The crude (2Z,5Z)-5-(3-chloro-4-((R)-2,3-dihydroxypropoxy)benzylidene)-2-(propylimino)-3-(o-tolyl)thiazolidin-4-one (10 g) is dissolved in acetonitrile (30 mL) at 70° C. The reaction mixture is cooled from 70° C. to 0° C. over 2 h. During the cooling ramp, (2Z,5Z)-5-(3-chloro-4-((R)-2,3-dihydroxypropoxy)benzylidene)-2-(propylimino)-3-(o-tolyl)thiazolidin-4-one seeds of crystalline form C (0.0075 g, 0.00075 eq.) are added at 50° C. The suspension is heated up to 52° C., cooled to 0° C. over 6 h and agitated at this temperature for 2 h. The product is filtered and washed with acetonitrile at −10° C. (2×12.8 mL).

Recrystallisation II: The wet product is dissolved in acetonitrile (27.0 mL) at 70° C. The reaction mixture is cooled from 70° C. to 0° C. over 2 h. During the cooling ramp, (2Z,5Z)-5-(3-chloro-4-((R)-2,3-dihydroxypropoxy)benzylidene)-2-(propylimino)-3-(o-tolyl)thiazolidin-4-one seeds of crystalline form C (0.0075 g, 0.00075 eq.) are added at 50° C. The suspension is heated up to 52° C., cooled to 0° C. over 6 h and agitated at this temperature for 2 h. The product is filtered and washed with acetonitrile at −10° C. (2×11.3 mL).

Recrystallisation III: The wet product is dissolved in acetonitrile (24.3 mL) at 70° C. The reaction mixture is cooled from 70° C. to 0° C. over 2 h. During the cooling ramp, (2Z,5Z)-5-(3-chloro-4-((R)-2,3-dihydroxypropoxy)benzylidene)-2-(propylimino)-3-(o-tolyl)thiazolidin-4-one seeds of crystalline form C (0.0075 g, 0.00075 eq.) are added at 50° C. The suspension is heated up to 52° C., cooled to 0° C. over 6 h and agitated at this temperature for 2 h. The product is filtered and washed with acetonitrile at −10° C. (2×10.1 mL).

Recrystallisation IV: The wet product is dissolved in acetonitrile (21.9 mL) at 70° C. The reaction mixture is cooled from 70° C. to 0° C. over 2 h. During the cooling ramp, (2Z,5Z)-5-(3-chloro-4-((R)-2,3-dihydroxypropoxy)benzylidene)-2-(propylimino)-3-(o-tolyl)thiazolidin-4-one seeds of crystalline form C (0.0075 g, 0.00075 eq.) are added at 50° C. The suspension is heated up to 52° C., cooled to 0° C. over 6 h and agitated at this temperature for 2 h. The product is filtered and washed with acetonitrile at −10° C. (2×9.1 mL).

Recrystallisation V: The wet product is dissolved in acetonitrile (19.7 mL) at 70° C. The reaction mixture is cooled from 70° C. to 0° C. over 2 h. During the cooling ramp, (2Z,5Z)-5-(3-chloro-4-((R)-2,3-dihydroxypropoxy)benzylidene)-2-(propylimino)-3-(o-tolyl)thiazolidin-4-one seeds of crystalline form C (0.0075 g, 0.00075 eq.) are added at 50° C. The suspension is heated up to 52° C., cooled to 0° C. over 6 h and agitated at this temperature for 2 h. The product is filtered and washed with acetonitrile at −10° C. (2×8.2 mL).

Recrystallisation VI: The wet product is dissolved in acetonitrile (23.9 mL) at 70° C. Water (20 mL) is added at 70° C. The reaction mixture is cooled from 70° C. to 0° C. over 2 h. During the cooling ramp, (2Z,5Z)-5-(3-chloro-4-((R)-2,3-dihydroxypropoxy)benzylidene)-2-(propylimino)-3-(o-tolyl)thiazolidin-4-one seeds of crystalline form C (0.0075 g, 0.00075 eq.) are added at 50° C. The suspension is heated up to 52° C., cooled to 0° C. over 6 h and agitated at this temperature for 2 h. The product is filtered and washed twice with a mixture of acetonitrile (4.5 mL) and water (4.5 mL) at −10° C.

The product is dried under vacuum at 45° C. for 24 h to afford a pale yellow solid; yield: 7.0 g (70%).

Example 2

(R)-3-Chloro-4-(2,3-dihydroxypropoxy)-benzaldehyde

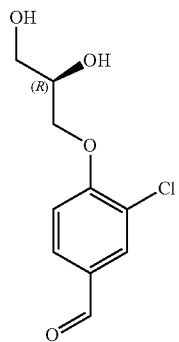

Potassium tert-butoxide (118 g, 1.20 eq.) is added to n-propanol (963 mL) followed by 3-chloro-4-hydroxybenzaldehyde (137 g, 1.00 eq.). To the mixture is added (R)-3-chloro-1,2-propanediol (126 g, 1.30 eq.). The suspension is heated to 90° C. and stirred at this temperature for 17 h. Solvent (500 mL) is distilled off at 120° C. external temperature and reduced pressure. Water is added (1.1 L) and solvent (500 mL) is removed by distillation. The turbid solution is cooled to 20° C. After stirring for one hour a white suspension is obtained. Water (500 mL) is added and the suspension is cooled to 10° C. The suspension is filtered and the resulting filter cake is washed with water (500 mL). The product is dried at 50° C. and reduced pressure to yield 149 g of a white solid (73%), which is (R)-3-chloro-4-(2,3-dihydroxypropoxy)-benzaldehyde in crystalline form A.

Example 3

(R)-3-Chloro-4-(2,3-dihydroxypropoxy)-benzaldehyde

Potassium tert-butoxide (8.60 g, 1.20 eq.) is added to n-propanol (70 mL) below 15° C., the temperature is allowed to rise. After the addition the temperature is corrected again to below 15° C. before addition of 3-chloro-4-hydroxybenzaldehyde (10 g, 1.00 eq.). The suspension is heated to 40° C. and stirred for 30 min. (R)-3-Chloro-1,2-propanediol (9.18 g, 1.30 eq.) is added at 40° C. The resulting suspension is heated to 60° C. and stirred at this temperature for 15 h then heated to 94° C. till meeting the IPC-specification (specification conversion ≥90.0%). The mixture is cooled to 30° C. and n-propanol is partially distilled off (~50 mL are distilled off) under reduced pressure and a maximum temperature of 50° C., the jacket temperature is not allowed to raise above 60° C.

Water (81 mL) is added and a second distillation is performed under the same conditions (24 mL are distilled off). The mixture is heated till homogeneous (maximum 54° C.) and then cooled to 24° C. At 24° C. the mixture is seeded with crystalline (R)-3-chloro-4-(2,3-dihydroxypropoxy)-benzaldehyde of form A (0.013 g, 0.00085 eq.). How to obtain the crystalline seeds is described in Examples 2 and 5. The reaction mixture is cooled to 0° C. over 7.5 h.

The product is filtered and washed with water (2×35 mL) and once with methyl tert-butyl ether (20 mL) at 5° C. The product is dried under vacuum at 40° C. for 20 h to afford an off-white solid; yield: 10.6 g (72%), which is (R)-3-chloro-4-(2,3-dihydroxypropoxy)-benzaldehyde in crystalline form A.

Example 4

(2Z,5Z)-5-(3-Chloro-4-((R)-2,3-dihydroxypropoxy) benzylidene)-2-(propylimino)-3-(o-tolyl)thiazolidin-4-one a) Preparation of crude (2Z,5Z)-5-(3-chloro-4-((R)-2,3-dihydroxypropoxy)benzylidene)-2-(propylimino)-3-(o-tolyl)thiazolidin-4-one n-Propylamine (5.23 g, 1.32 eq.) is added to a solution of o-tolyl-iso-thiocyanate (10 g, 1.00 eq.) in dichloromethane (100 mL) at 20° C. The resulting pale yellow solution is agitated for 15 min at 20° C. before IPC (conversion specification ≥99.0%). The reaction is cooled to −2° C. Bromoacetyl bromide (14.88 g, 1.10 eq.) is added and the resulting solution is stirred for 15 min at −2° C. Pyridine (10.92 g, 2.05 eq.) is then added slowly at −2° C. The intensive yellow reaction mixture is stirred for 15 min at −2° C. before IPC (conversion specification 93.0%). Dichloromethane is partially distilled off (66 mL are distilled off) under atmospheric pressure and jacket temperature of 60° C. Ethanol (111.4 mL), sodium acetate (12.75 g, 2.30 eq.) and (R)-3-chloro-4-(2,3-dihydroxypropoxy)-benzaldehyde from Example 3 (14.38 g, 0.93 eq.) are added. The remaining dichloromethane and a part of ethanol are distilled off (49.50 mL are distilled off) under atmospheric pressure and jacket temperature up to 85° C. The reaction mixture (orange suspension) is stirred for 3-5 h under reflux (78° C.) before IPC (conversion specification ≥97.0%).

Water (88.83 mL) is added and the temperature adjusted to 40° C. before seeding with micronized (2Z,5Z)-5-(3-chloro-4-((R)-2,3-dihydroxypropoxy)benzylidene)-2-(propylimino)-3-(o-tolyl)thiazolidin-4-one in crystalline form C (0.075 g, 0.0024 eq.). The reaction mixture is cooled to 0° C. over 5 h, heated up to 40° C., cooled to 0° C. over 6 h and stirred at this temperature for 2 h.

The product is filtered and washed with a 1:1 ethanol:water mixture (2×48 mL) at 0° C. The product is dried under vacuum at 45° C. for 10 h to afford a pale yellow solid; yield: 24.71 g (86%).

b) Purification of (2Z,5Z)-5-(3-chloro-4-((R)-2,3-dihydroxypropoxy)benzylidene)-2-(propylimino)-3-(o-tolyl)thiazolidin-4-one The crude (2Z,5Z)-5-(3-chloro-4-((R)-2,3-dihydroxypropoxy)benzylidene)-2-(propylimino)-3-(o-tolyl)thiazolidin-4-one (10 g) is dissolved in ethanol (40 mL) at 70° C. The temperature is adjusted at 50° C. for seeding with micronised (2Z,5Z)-5-(3-chloro-4-((R)-2,3-dihydroxypropoxy)benzylidene)-2-(propylimino)-3-(o-tolyl)thiazolidin-4-one in crystalline form C (0.016 g, 0.0016 eq.). The reaction mixture is cooled from 50° C. to 0° C. over 4 h, heated up to 50° C., cooled to 0° C. over 6 h and agitated at this temperature for 2 h. The product is filtered and washed with ethanol at 0° C. (2×12.8 mL). The product is dried under vacuum at 45° C. for 10 h to afford a pale yellow solid; yield: 9.2 g (92%).

Example 5

Preparation of crystalline seeds of (R)-3-chloro-4-(2,3-dihydroxypropoxy)-benzaldehyde 10 mg of (R)-3-chloro-4-(2,3-dihydroxypropoxy)-benzaldehyde of at least 99.5% purity by 1H-NMR assay is dissolved in a 4 mL vial by adding 1 mL of pure ethanol (puriss p.a.). The solvent is allowed to evaporate through a small hole in the cap (approx. 2 mm of diameter) of the vial until complete dryness. The white solid residue is crystalline (R)-3-chloro-4-(2,3-dihydroxypropoxy)-benzaldehyde in crystalline form A. Alternatively, methanol or methylisobutylketone (both in puriss p.a. quality) is used. This procedure is repeated until sufficient seeds are made available.

TABLE 5

Characterisation data for crystalline form A of (R)-3-chloro-4-(2,3-dihydroxypropoxy)-benzaldehyde

| Technique | Data Summary | Remarks |
|---|---|---|
| XRPD | Crystalline | see FIG. 1 |
| DSC | Endotherm (melt): Melting point of about 94° C. reported as peak temperature | |

The invention claimed is:

1. A process for the preparation of (R)-3-chloro-4-(2,3-dihydroxypropoxy)-benzaldehyde (1):

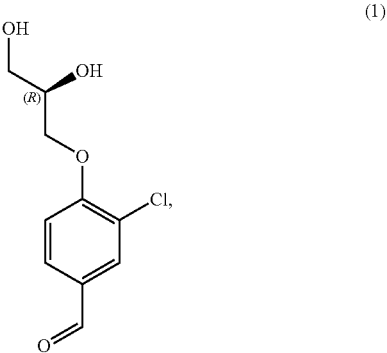

which process comprises reacting 3-chloro-4-hydroxybenzaldehyde with (R)-3-chloro-1,2-propanediol and isolating the obtained (R)-3-chloro-4-(2,3-dihydroxypropoxy)-benzaldehyde by crystallisation.

2. The process according to claim 1, wherein the reaction of 3-chloro-4-hydroxybenzaldehyde with (R)-3-chloro-1,2-propanediol is performed in the presence of the base potassium tert-butoxide and the solvent n-propanol, at elevated temperatures.

3. The process according to claim 1, wherein the obtained (R)-3-chloro-4-(2,3-dihydroxypropoxy)-benzaldehyde (1) is crystallised in water plus a co-solvent.

4. The process according to claim 3, wherein the co-solvent is n-propanol.

5. The process according to claim 1, further comprising reacting the obtained (R)-3-chloro-4-(2,3-dihydroxypropoxy)-benzaldehyde (1) with 2-[(Z)-propylimino]-3-o-tolyl-thiazolidin-4-one to form (2Z,5Z)-5-(3-chloro-4-((R)-2,3-dihydroxypropoxy)benzylidene)-2-(propylimino)-3-(o-tolyl)thiazolidin-4-one (2):

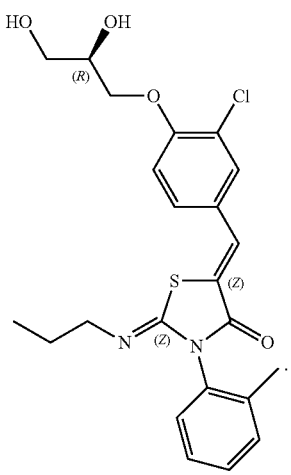

6. The process according to claim 5, wherein 2-[(Z)-propylimino]-3-o-tolyl-thiazolidin-4-one is prepared by reacting o-tolyl-iso-thiocyanate with n-propylamine followed by reaction with bromo-acetyl bromide and the base pyridine, wherein no isolation and/or purification of intermediates occurs and wherein the obtained 2-[(Z)-propylimino]-3-o-tolyl-thiazolidin-4-one is not isolated and/or purified before the reaction with (R)-3-chloro-4-(2,3-dihydroxypropoxy)-benzaldehyde (1).

7. The process according to claim 6, wherein (R)-3-chloro-4-(2,3-dihydroxypropoxy)-benzaldehyde (1) is reacted with 2-[(Z)-propylimino]-3-o-tolyl-thiazolidin-4-one in the presence of the solvent ethanol and the base sodium acetate, at elevated temperatures.

8. The process according to claim 5, characterised in that (R)-3-chloro-4-(2,3-dihydroxypropoxy)-benzaldehyde (1) is isolated by a single crystallisation before the reaction with 2-[(Z)-propylimino]-3-o-tolyl-thiazolidin-4-one.

9. The process according to claim 5, wherein in a first isolation step the obtained compound (2) is isolated by crystallisation.

10. The process according to claim 9, wherein the compound (2) obtained after the first isolation step is in the crystalline form characterised by the presence of peaks in the X-ray powder diffraction diagram at the following angles of refraction 2θ: 10.5°, 11.1°, 11.4°, 13.6°, 13.9°, 16.3°, 20.8°, 22.2°, 23.4°, 24.1°, 25.7°, 27.7°, 27.9°, 28.7°, and 29.3°, wherein the X-ray powder diffraction diagram is obtained by using Cu Kα1 radiation (λ=1.5406 Å) and stripping of the Kα2 component and wherein the accuracy of the 2θ values is in the range of +/−0.2°.

11. The process according to claim 9, wherein the obtained crystalline compound (2) is further purified by one or more recrystallisation steps.

12. The compound (R)-3-chloro-4-(2,3-dihydroxypropoxy)-benzaldehyde in crystalline form.

13. The crystalline form according to claim 12, characterised by the presence of peaks in the X-ray powder diffraction diagram at the following angles of refraction 2θ: 7.3°, 9.7°, 12.7°, 13.3°, 19.6°, 22.1°, 27.9°, and 28.5°, wherein the X-ray powder diffraction diagram is obtained by using Cu Kα1 radiation (λ=1.5406 Å) and stripping of the Kα2 component and wherein the accuracy of the 2θ values is in the range of +/−0.2°.

14. The crystalline form according to claim 12, which has a melting point of about 94° C. as determined by differential scanning calorimetry.

15. A crystalline form of the compound (R)-3-chloro-4-(2,3-dihydroxypropoxy)-benzaldehyde obtainable by:
  i) adding potassium tert-butoxide (118 g, 1.20 eq.) to n-propanol (963 mL) followed by 3-chloro-4-hydroxy-benzaldehyde (137 g, 1.00 eq.);
  ii) adding to the mixture (R)-3-chloro-1,2-propanediol (126 g, 1.30 eq.), heating the suspension to 90° C. and stirring it at this temperature for 17 h;
  iii) distilling off the solvent (500 mL) at 120° C. external temperature and reduced pressure;
  iv) adding water (1.1 L) and removing solvent (500 mL) by distillation;
  v) cooling the turbid solution to 20° C. and stirring for one hour to obtain a white suspension;
  vi) adding water (500 mL) and cooling the suspension to 10° C.;
  vii) filtering the suspension and washing the resulting filter cake with water (500 mL); and
  viii) drying the product at 50° C. and reduced pressure.

16. The crystalline form according to claim 15, which has a melting point of about 94° C. as determined by differential scanning calorimetry.

17. A process for the preparation of (2Z,5Z)-5-(3-chloro-4-((R)-2,3-dihydroxypropoxy)benzylidene)-2-(propylimino)-3-(o-tolyl)thiazolidin-4-one comprising the process according to claim 1.

18. The crystalline form according to claim 13, which has a melting point of about 94° C. as determined by differential scanning calorimetry.

* * * * *